Oct. 19, 1965 C. FISCHER Plant Pat. 2,559
GLADIOLUS PLANT
Filed Feb. 27, 1964
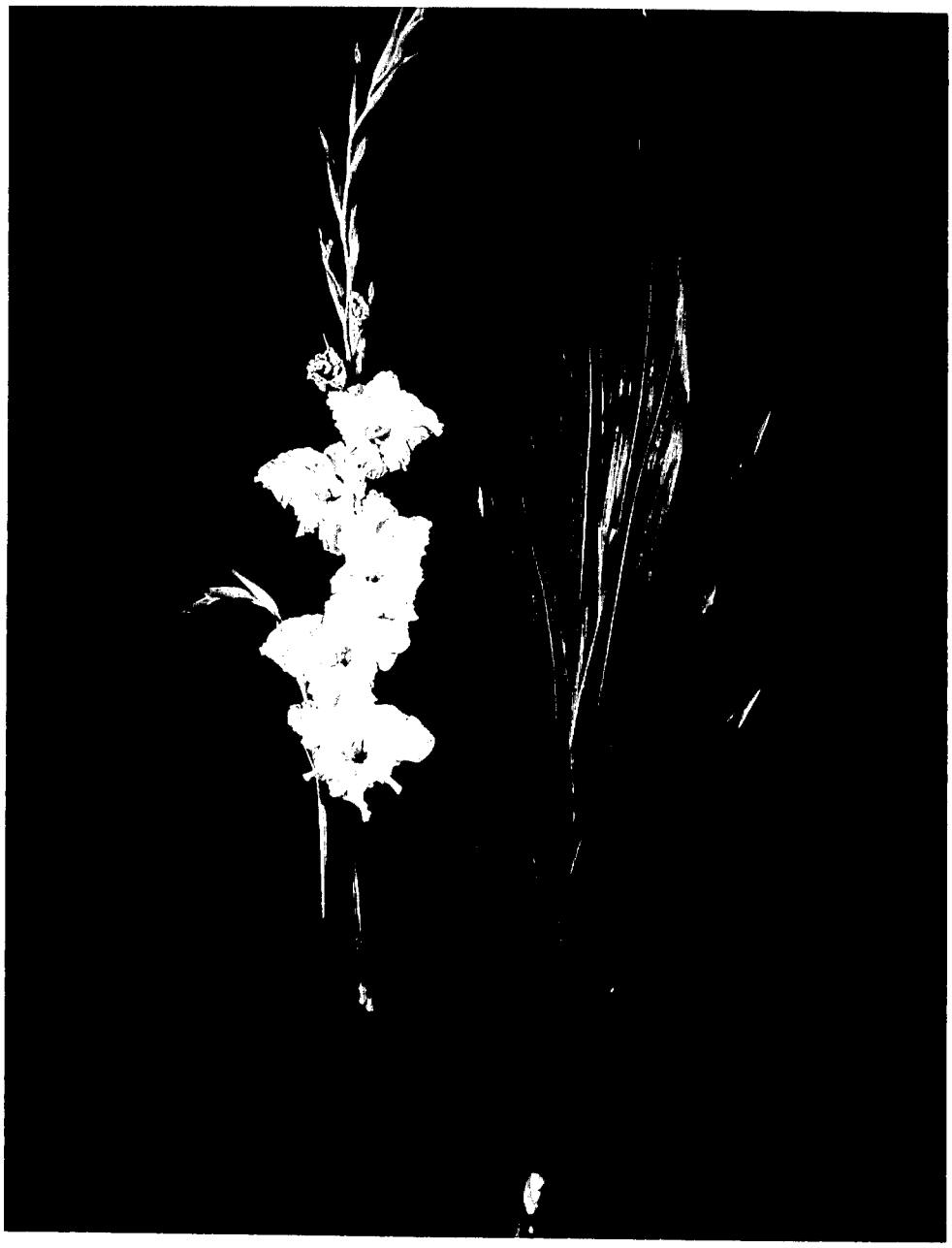
Inventor.
Carl Fischer
By: Robb & Robb
Attorneys United States Patent Office Plant Pat. 2,559
Patented Oct. 19, 1965

2,559
GLADIOLUS PLANT

Carl Fischer, St. Charles, Minn., assignor to Imperial Flowers Limited, Leamington, Ontario, Canada, a corporation of Canada Filed Feb. 27, 1964, Ser. No. 347,982
1 Claim. (Plt.—85)

The present invention relates to a new and distinct variety of gladiolus plant which was originated by me by crossing an unnamed and unpatented variety derived from a cross of "Fire Opal" × "Pactolus" (both unpatented) with an unnamed and unpatented yellow seedling of unidentified parentage, the former being the seed parent and the unnamed yellow seedling being the pollen parent.

As the result of this breeding, I have produced a new and improved gladiolus variety, as evidenced by the following unique combination of characteristics which are outstanding therein and which distinguish it from its parents, as well as from all other varieties of which I am aware:

(1) A rugged and vigorous habit of growth;
(2) The production of smooth, clean bulbs; and
(3) Distinctive and attractive greenish-yellow ruffled flowers.

My new variety resembles the variety known as "Green Woodpecker" (unpatented) more than any other, but principally differs therefrom by having a taller habit of growth; needle-pointed flowers which are more ruffled in form; more self-coloring in the flowers; the production of cleaner and healthier bulbs; and heavier propagation qualities.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen plant of my new variety, including the foliage and bulb, and a separate typical flower spike, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Extremely rugged; excellent propagator.

Blooming habit: Comes into bloom from large bulbs in about 85 days in the northern latitudes of the United States.

Stems: Very slender.
*Diameter at base.*—From about ¼ inch to ⅜ inch.
*Color (at base).*—White.

Foliage: Upright; leaves average about 1½ inches wide and attain a height of from 36 inches to 40 inches. Color—deep green.

Disease resistance: Extremely resistant to all known gladiolus diseases, as determined by comparison with other varieties grown in my fields near St. Charles, Minnesota.

Corms (bulbs): High-crowned; round; smooth. Color of flesh—ivory.

*Flower*

Spike: Blossom spike averages about 55 inches tall, with flower-head ranging from about 20 inches to 22 inches long; bears 15 buds on the average, with 4 or 5 buds open at one time.

Bud:
*Size.*—About 2½ inches long when opening.
*Opening.*—Usually 3 buds show color at one time.

Flower:
*Arrangement.*—Florets are informally arranged on the stem.
*Size.*—Individual florets average 4¼ inches in diameter.
*Form.*—Florets are ruffled, triangular, and have a somewhat butterfly type form.
*Keeping qualities.*—Average.

Petals:
*Shape.*—Outer petals are somewhat pointed and creased at edges.
*Size.*—Upper petals—about 2 inches wide. Lip petal—about 1¼ inches wide.
*Aspect.*—Heavy substance; irregular surface due to ruffling.
*Fragrance.*—None.
*Color.*—General color effect is Uranium Green, Plate 63/3, with opening bud and freshly open florets being Uranium Green, Plate 63/2; throat of lip petal has purple sanding which is heavier at the calyx; color is deeper on the lip petals.

*Reproductive organs*

Stamens: Color—cream.
Pistils: Color—cream.

I claim:

A new and distinct variety of gladiolus plant, substantially as herein shown and described, characterized particularly as to novelty by the unique combination of a rugged and vigorous habit of growth, the production of smooth and clean bulbs, and ruffled flowers having a distinctive and attractive greenish yellow general color tonality.

No references cited.

ABRAHAM G. STONE, *Primary Examiner.*